United States Patent [19]
Spangle

[11] 3,981,202
[45] Sept. 21, 1976

[54] APPARATUS FOR MEASURING THE DENSITY OF A CEMENT SLURRY

[75] Inventor: Lloyd B. Spangle, Tulsa, Okla.

[73] Assignee: The Dow Chemical Company, Midland, Mich.

[22] Filed: Jan. 2, 1975

[21] Appl. No.: 537,872

[52] U.S. Cl. ............................................. 73/438
[51] Int. Cl.² .................................... G01N 9/26
[58] Field of Search ...................... 73/438, 205 D

[56] References Cited
UNITED STATES PATENTS

| | | | |
|---|---|---|---|
| 2,287,027 | 6/1942 | Cummins, Jr. | 73/438 X |
| 2,768,529 | 10/1956 | Hagler, Sr. | 73/438 |
| 3,175,403 | 3/1965 | Nelson | 73/438 |
| 3,473,401 | 10/1969 | Fajans et al. | 73/438 |
| 3,554,011 | 1/1971 | Van DerVeen | 73/438 X |
| 3,926,050 | 12/1975 | Turner et al. | 73/438 X |

Primary Examiner—Herbert Goldstein
Assistant Examiner—John S. Appleman
Attorney, Agent, or Firm—V. Dean Clausen

[57] ABSTRACT

In a specific application the apparatus of this invention is used to measure the density of cement slurries employed in oil well cementing operations. As the slurry stream is pumped to the bore hole it is split into two parts. One part of the stream is sent through a curved conduit section which is positioned horizontally. The remaining part of the stream travels through a curved conduit section which is in a vertical position. The slurry flow in the vertical conduit sets up a hydrostatic pressure differential between the streams. This pressure difference, which is sensed by a differential pressure indicator, is read directly as units of density on the indicator scale.

1 Claim, 3 Drawing Figures

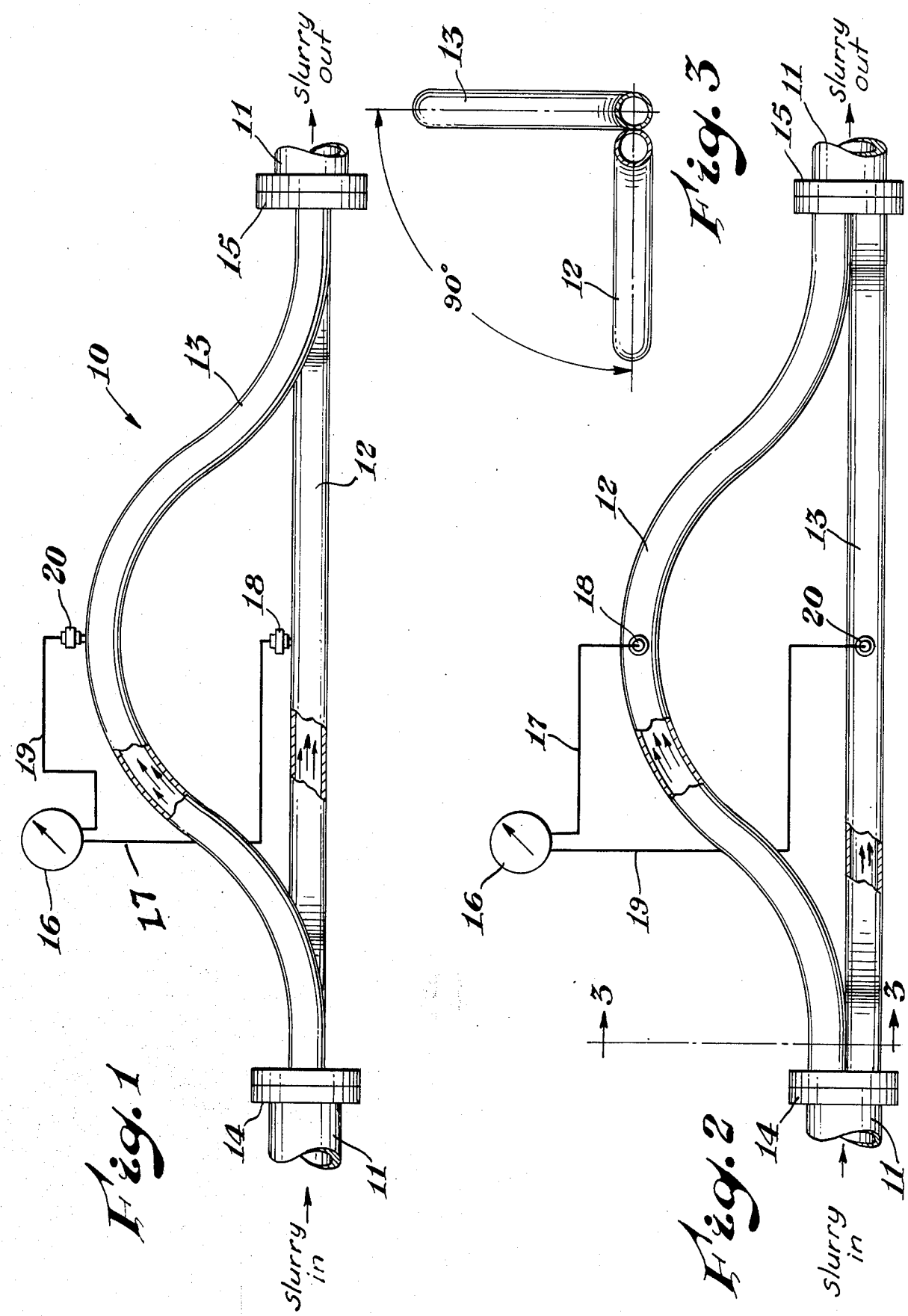

APPARATUS FOR MEASURING THE DENSITY OF A CEMENT SLURRY

BACKGROUND OF THE INVENTION

Broadly, the invention relates to density measurements of liquids. More specifically, the invention is directed to measuring the density of a flowing liquid.

There are many industrial operations and processes in which the success of the operation depends on reliable measurement of the density of a liquid. An example of such an operation is the cementing of a borehole for an oil well. In this operation the cement, as a slurry, is injected into an annulus formed between the pipe casing and the wall of the borehole. When the slurry reaches the desired location in the borehole it is allowed to harden.

To achieve a satisfactory job in oil well cementing, it is extremely important to closely regulate the density of the cement slurry during the injection operation. The density of a cement slurry is a measure of the amount of water used with a sack of dry cement material. The amount of water in the slurry controls many physical properties of the cement. For example, too much water can increase the thickening and setting time of the cement beyond a desirable period. An excess of water in the slurry can also cause shrinkage which will weaken the set cement. In addition, too much water can cause pockets of water to form behind the pipe casing. By contrast, if the slurry contains too little water it will increase initial viscosity and thixotropy of the cement and cause plug flow or a preliminary flash setting.

A conventional instrument widely used in oil field work to measure cement slurry density is called a cement densitometer. The instrument is made up essentially of three elements, namely, a radioactive source, a radiation detector, and an automatic recorder. Briefly, the operation of the instrument involves passing gamma rays from the radioactive source through the cement slurry stream. Part of the gamma radiation is absorbed by the slurry and the unabsorbed portion is measured by a gamma ray detection cell. The radioactive energy absorbed by the slurry is proportional to the slurry density. The energy readings are continuously recorded on a strip chart, with the chart being calibrated to read directly as slurry weight, i.e. in pounds per gallon v. time.

The cement densitometer described above has certain disadvantages. One drawback of this instrument is that it can give different readings for cement slurries which have essentially the same density. The reason for the variance is that the additive content of each slurry composition may vary. For example, some slurry compositions may contain cellulose materials, which function as retarder compositions. Other slurry compositions may contain chloride compounds, which act as accelerator compositions. When the gamma radiation passes through each of the slurries mentioned above the actual absorption will be different for the cellulose material than it is for the chloride compounds. The result is that the density reading on the strip chart may be quite different for the two slurry compositions, but the true density may be very nearly the same. To obtain an accurate density reading, therefore, the instrument must be calibrated for each slurry composition which is measured.

The densitometer described above has another disadvantage in that the operation of the instrument is sufficiently complex to require a highly skilled operator. Another disadvantage of this instrument is the possibility of exposure of the operator to harmful radiation.

SUMMARY OF THE INVENTION

In a specific application the instrument of this invention is used to measure the density of a liquid stream, such as a cement slurry, during injection of the slurry into the borehole of an oil well. In operation, the liquid stream is passed through a delivery conduit, at a positive pressure, from a holding point to a use point. While enroute to the use point the liquid stream is diverted from the delivery conduit and passed through two separate conduit sections in communication with the delivery conduit. Part of the stream follows a horizontal curved path through one of the conduit sections. The remaining part of the stream follows a vertical curved path through the other conduit section.

The stream part which passes through the horizontal conduit section is under a higher pressure than the stream part which passes through the vertical conduit section. A pressure difference which exists between the horizontal stream path and the vertical stream path is a direct indication of the density of the liquid. This pressure difference is measured by a differential pressure indicator, which connects into both the high pressure conduit section and the low pressure conduit section. The pressure difference sensed by the indicator can be read directly as units of density on the indicator scale.

DESCRIPTION OF THE DRAWING

FIG. 1 is a side elevation view, partly in section, of one embodiment of the density measuring apparatus of this invention.

FIG. 2 is a plan view, partly in section, of the density measuring apparatus shown in FIG. 1.

FIG. 3 is a cross section view of the density measuring apparatus, as taken on line 3—3 of FIG. 2.

DESCRIPTION OF A PREFERRED EMBODIMENT

In the drawing the numeral 10 refers generally to an apparatus for measuring the density of liquids. To illustrate the practice of the invention the apparatus 10 is described as it would operate in measuring the density of a cement slurry. In this instance the slurry is being used to cement the borehole of an oil well.

In a typical oil well cementing operation the slurry is mixed and blended at the well site and then pumped under pressure into the borehole. From the pumper truck (not shown) the slurry is carried through a delivery conduit 11 and into the well head (not shown). As explained above, it is necessary to continuously monitor the density of the cement slurry to achieve a satisfactory cementing job in the well. In the present invention the main slurry stream which is being conducted through conduit 11 is separated into two identical stream parts at a point between the pumper truck and the well head. The objective is to create an apparatus in which a different pressure force will act on each of the separated stream parts at a given point. More specifically, the pressure force acting on one stream will be a higher pressure than that acting on the other stream. By measuring the difference between the two pressures, therefore, the density of the slurry can be calculated.

Means for separating the main slurry stream into separate stream parts is provided by a first conduit section 12 and a second conduit section 13. The conduit sections 12 and 13 are connected at each end into the delivery conduit 11 by swivel couplings 14 and 15. The conduit sections 12 and 13 are identical in shape, length and cross-sectional area. A preferred shape for each conduit section is a gentle curve, as indicated in FIGS. 1 and 2. When the density measuring apparatus 10 is in operating position, the conduit section 12 will lie in the horizontal plane. For conduit section 13, which is positioned at 90° from conduit section 12, the operating position will be in the vertical plane.

As the cement slurry is pumped to the well head, part of the main stream will follow the horizontal curved path of conduit section 12. The remaining part of the slurry stream will follow the vertical curved path of conduit section 13. The point of lowest pressure on the slurry stream will be at the uppermost point of the curve in conduit section 13. The actual pressure at this point will be that pressure which is required to pump the slurry from the pumper truck to the well. Typical slurry pumping pressure is about 20 psi. Understandably, the actual pressure will depend on several factors, such as the composition of the cement slurry, the distance from the pumper truck to the well head, the size of the delivery conduit, and the like.

The higher pressure acting on the slurry stream will be at a point somewhere in conduit section 12. A preferred point for measuring the higher pressure is at the outermost point of the curve in conduit section 12. In conduit section 12 the higher pressure exerted on the slurry stream results from a combination of hydrostatic pressure and the actual pumping pressure. In this instance the hydrostatic pressure results from the liquid head created by lifting part of the slurry stream, that part flowing through conduit section 13, a given vertical distance above the slurry stream in conduit section 12.

A differential pressure indicator 16 is used to measure the pressure difference between the slurry streams in the conduit sections 12 and 13. A suitable instrument for this purpose is a conventional differential pressure gauge of the type used to measure water pressure. On gauges for measuring water pressure, units on the dial represent inches of water (height). In the practice of this invention the gauge is modified so that the hydrostatic pressure differential sensed by the gauge will read directly as units of density. The density units for cement slurries are expressed as pounds per gallon. For example, typical slurries for cementing oil wells will run from about 13 to 17 pounds per gallon. The pound units in this case represent the actual mix weight for each gallon of pumpable cement slurry.

The differential pressure gauge 16 has two connections. One connection is for high pressure input, the other is for low pressure input. A line 17 connects the high pressure area of gauge 16 to a hydraulic isolation diaphragm plug 18, at the outer point of conduit section 12. Another line 19 connects the low pressure area of gauge 16 to a similar diaphragm plug 20, at the upper point of conduit section 13. The lines 17 and 19 comprise small diameter tubing. In general, the tubing can be fabricated of flexible materials which do not readily expand under applied pressure. Examples of suitable tubing materials are plastic resins, such as Teflon, vinyl compounds, such as Tygon, and copper tubing.

Where the apparatus 10 is used to measure density of a cement slurry, the pressure exerted by the slurry stream in both conduit sections 12 and 13 will act against one side of a diaphragm member (not shown) which is seated in the diaphragm plugs 18 and 20. The opposite side of each diaphragm member transmits the pressure force through a fluid, such as air, which is contained in the lines 17 and 19. The fluid in line 17 transmits the pressure force into the high pressure area of gauge 16. Similarly, the fluid in line 19 transmits the pressure force to the low pressure area of gauge 16.

Various details regarding the structure and operation of the present density measuring apparatus will now be described. These engineering details will apply generally to an apparatus useful for measuring the density of cement slurries. Understandably, modifications of these structural and operational details might be desirable where the present apparatus is used to measure density of liquids other than cement slurries.

The total cross sectional area of the conduit sections 12 and 13 should not exceed the cross sectional area of delivery conduit 11. This applies to both the slurry inlet connection at swivel coupling 14 and the slurry outlet connection at swivel coupling 15. One reason for this requirement is to prevent a change in velocity of the slurry when it enters the conduit sections 12 and 13 at coupling 14 and when it exits from the conduit sections at coupling 15. Another reason for this requirement is to prevent solids from dropping out of the cement slurry as it passes through the coupling connections 14 and 15.

As mentioned above, the conduit sections 12 and 13 are formed in the shape of a minor or gentle curve. The objective is to provide conduits in which the slurry will flow in a streamline pattern. The actual shape of the conduit sections 12 and 13 is not critical, but a streamline configuration is desirable to prevent any restriction or obstruction of the slurry flow. For example, if the slurry flow through the conduit sections is interrupted, density measurement will be inaccurate. In addition, each of the conduit sections 12 and 13 must be identical in shape (curvature) and the cross sectional area and length of each conduit section must be the same. The reason for this requirement is so that each conduit section will have the same volume; otherwise, the density reading will be in error.

A horizontal level indicator (not shown) should be installed on the conduit section 12. A level indicator of the type used on a laboratory balance is suitable for this purpose. The function of the level indicator is to keep the conduit section 12 in a horizontal plane. For example, if the conduit section 12 is allowed to tilt above or below the horizontal, the hydrostatic pressure created by the slurry flow through conduit section 13, will not approximate the true hydrostatic pressure exerted by the slurry in the borehole.

In this invention a simple and convenient calibration and accuracy test can be made in the field by using water. The procedure involves pumping water at a given pressure through the conduit sections 12 and 13 and observing the density reading on gauge 16. In this instance, the pressure differential sensed by the gauge will correspond to the density of the water as measured by the height difference between the water flow in conduit section 12 and conduit section 13.

The invention claimed is:
1. Apparatus for measuring the density of a cement slurry stream, which includes the combination of:
a delivery conduit which is adapted for carrying the cement slurry stream under a positive pressure from a holding point to a use point, the delivery conduit being connected at one end to the holding point and at the other end to the use point;
a first conduit section which communicates with the delivery conduit, which has a curved shape, which is in a horizontal position, and which is adapted to carry in a horizontal curved path a part of the cement slurry stream which is enroute to the use point;
a second conduit section which communicates with the delivery conduit, which has a curved shape, which is in a vertical position located at 90° from the horizontal position of the first conduit section, and which is adapted to carry in a vertical curved path a part of the cement slurry stream which is enroute to the use point;
the combined cross-sectional area of the first conduit section and the second conduit section being an area not greater than the cross-sectional area of the delivery conduit;
a differential pressure indicator having a high pressure area which communicates with the first conduit section, a low pressure area which communicates with the second conduit section, and a scale which reads in units of density, wherein
the said pressure indicator will sense a pressure difference between the part of the slurry stream flowing through the first conduit section and the part of the slurry stream flowing through the second conduit section, and will read the said pressure difference on the indicator scale as units of density.

* * * * *